(12) United States Patent
Son et al.

(10) Patent No.: US 10,414,776 B2
(45) Date of Patent: Sep. 17, 2019

(54) EFFICIENT METHOD FOR PRODUCING AND PURIFYING ANHYDROUS SUGAR ALCOHOL

(71) Applicant: SK Innovation Co., Ltd., Seoul (KR)

(72) Inventors: Sung Real Son, Daejeon (KR); In Hyoup Song, Daejeon (KR); Yoon Jae Yim, Sejong-si (KR); Suk Joon Hong, Daejeon (KR); Young Bo Choi, Seoul (KR)

(73) Assignee: SK Innovation Co., Ltd., Seoul (KR)

( * ) Notice: Subject to any disclaimer, the term of this patent is extended or adjusted under 35 U.S.C. 154(b) by 55 days.

(21) Appl. No.: 15/538,301

(22) PCT Filed: Dec. 23, 2015

(86) PCT No.: PCT/KR2015/014139
§ 371 (c)(1),
(2) Date: Jun. 21, 2017

(87) PCT Pub. No.: WO2016/105107
PCT Pub. Date: Jun. 30, 2016

(65) Prior Publication Data
US 2017/0349603 A1 Dec. 7, 2017

(30) Foreign Application Priority Data
Dec. 23, 2014 (KR) .................... 10-2014-0187271

(51) Int. Cl.
| | | |
|---|---|---|
| *C07H 1/00* | (2006.01) | |
| *C07D 493/04* | (2006.01) | |
| *B01D 3/00* | (2006.01) | |
| *B01D 9/00* | (2006.01) | |
| *B01J 14/00* | (2006.01) | |
| *B01D 3/10* | (2006.01) | |

(52) U.S. Cl.
CPC ........... *C07D 493/04* (2013.01); *B01D 3/002* (2013.01); *B01D 3/009* (2013.01); *B01D 3/10* (2013.01); *B01D 9/0031* (2013.01); *B01J 14/00* (2013.01); *B01D 2009/0086* (2013.01); *C07B 2200/13* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 6,639,067 B1 | 10/2003 | Brinegar et al. | |
| 6,864,378 B2 * | 3/2005 | Bhatia .................. | C07D 493/04 |
| | | | 549/464 |
| 7,420,067 B2 * | 9/2008 | Sanborn ............... | C07D 307/02 |
| | | | 549/464 |
| 9,290,508 B2 * | 3/2016 | Kyung .................... | C07C 29/80 |
| 2011/0160479 A1 * | 6/2011 | Bianchi .................. | C07C 67/00 |
| | | | 560/174 |

FOREIGN PATENT DOCUMENTS

| | | |
|---|---|---|
| KR | 20010079763 A | 8/2001 |
| KR | 101079518 B1 | 11/2011 |
| KR | 1020130126303 A | 11/2013 |
| KR | 1020140048435 A | 4/2014 |
| KR | 1020140080748 A | 7/2014 |
| KR | 1020140105189 A | 9/2014 |

OTHER PUBLICATIONS

Jiang et al. Chemical Engineering Science (2012), vol. 84, pp. 120-133.*

* cited by examiner

*Primary Examiner* — Patrick T Lewis
(74) *Attorney, Agent, or Firm* — The Webb Law Firm

(57) ABSTRACT

The present invention relates to a method of producing and purifying a high-purity anhydrosugar alcohol in high yield by a simple process and apparatus, the method includes the steps of: allowing a sugar alcohol to react in the presence of an acid catalyst in a reactor, and, at the same time, evaporating a product of the reaction; cooling the evaporated product to remove water and obtain a crude anhydrosugar alcohol; and introducing the crude anhydrosugar alcohol into a melt crystallization process to obtain a high-purity anhydrosugar alcohol.

25 Claims, 10 Drawing Sheets

EFFICIENT METHOD FOR PRODUCING AND PURIFYING ANHYDROUS SUGAR ALCOHOL

CROSS-REFERENCE TO RELATED APPLICATIONS

This application is the United States national phase of International Application No. PCT/KR2015/014139 filed Dec. 23, 2015, and claims priority to Korean Patent Application No. 10-2014-0187271 filed Dec. 23, 2014, the disclosures of which are hereby incorporated in their entirety by reference.

TECHNICAL FIELD

The present invention relates to an effective method for production and purification of anhydrosugar alcohol, and more particularly to an effective method for production and purification of anhydrosugar alcohol, in which high-purity anhydrosugar alcohol is produced by simultaneously performing the production and distillation of anhydrosugar alcohol, and then performing a melt crystallization process.

BACKGROUND ART

Due to the exhaustion of traditional energy sources together with an increase in the global energy demand, impetus is currently being given to the development of alternative energy sources. Among them, biomass is renewable quantitative biological resource that attracts a great deal of attention.

Among biomass-based industrial raw materials, isosorbide ($C_6H_{10}O_4$) that is prepared by dehydration of sorbitol ($C_6H_{14}O_6$) attracts attention as an environmentally friendly raw material for preparing polycarbonate (PC) as a substitute for bisphenol A (BPA), an epoxy monomer or an environmentally friendly plasticizer. Namely, isosorbide, a material that can be obtained by simple dehydration of sorbitol, is attracting attention as a monomer required for synthesis of next-generation, high-performance, environmentally friendly materials that can replace conventional polymer products, and many studies thereon have been conducted.

Environmentally friendly materials generally show poor properties compared to petrochemical-based materials, whereas isosorbide advantages in that it is environmentally friendly and, at the same time, shows excellent properties compared to conventional petrochemical-based materials. In addition, isosorbide may be used as an additive that can make plastic materials stronger and tougher, and that is also used as an agent for treating cardiac diseases by being boded to nitrate.

When D-glucose obtained from biomass by pretreatment is hydrogenated in the presence of a catalyst, sorbitol is produced. Isosorbide is produced by double dehydration of sorbitol. This cyclization reaction is influenced by various reaction conditions, including temperature, pressure, solvent, catalyst, etc.

Currently, as a method of producing anhydrosugar alcohols, including isosorbide, a process is widely used in which sulfuric acid is used as a catalyst and a reaction is carried out under reduced pressure (Korean Patent No. 10-1079518). However, when a strong acid catalyst such as sulfuric acid is used, a reactor is easily corroded, and for this reason, an expensive reactor should be used in order to prevent the corrosion of the reactor. Furthermore, a large amount of energy is continuously consumed to maintain a vacuum level, and thus the production cost is increased. In addition, because it is not easy to manufacture a continuous vacuum reaction system with high reliability, most processes are carried out using a batch type or semi-batch type reactor.

Meanwhile, anhydrosugar alcohol has a high boiling point and is easily decomposed by high-temperature heat and thus anhydrosugar alcohol is difficult to separate by general atmospheric pressure distillation. For this reason, a vacuum distillation process is frequently used (U.S. Pat. No. 6,639,067). However, there is a disadvantage in that the production cost increases rapidly, because a vacuum level should be maintained not only in the reaction process, but also in the separation process, and because the yield of anhydrosugar alcohol decreases when a multi-step process is carried out.

Accordingly, the present inventors have conducted studies to solve the above-described problems, and as a result, have found that, if an anhydrosugar alcohol is produced by heating a reactor while supplying a mixture of a catalyst and a sugar alcohol to the reactor, and, at the same time, the anhydrosugar alcohol is separated by distillation, after which melt crystallization is performed, a high-purity anhydrosugar alcohol can be produced in high yield by a simple process, thereby completing the present invention.

SUMMARY OF INVENTION

It is an object of the present invention to provide a method for production and purification of anhydrosugar alcohol, which can increase the yield and purity of anhydrosugar alcohol in a reaction that produces and purifies anhydrosugar alcohol from sugar alcohol.

DETAILED DESCRIPTION OF THE INVENTION

To achieve the above object, the present invention provides a method of preparing and purifying anhydrosugar alcohol, the method comprises: reacting a sugar alcohol in a presence of an acid catalyst in a reactor, and at the same time, evaporating a reaction product; cooling an evaporated product, thereby obtaining a crude anhydrosugar alcohol; and introducing the crude anhydrosugar alcohol into a melt crystallization process, thereby obtaining a high-purity anhydrosugar alcohol.

The present invention also provides a method of preparing and purifying anhydrosugar alcohol, the method comprises: reacting a sugar alcohol in a presence of an acid catalyst in a reactor, and at the same time, evaporating a reaction product; cooling an evaporated product, thereby obtaining a crude anhydrosugar alcohol; adsorbing the crude anhydrosugar alcohol; and introducing an adsorbed crude anhydrosugar alcohol into a melt crystallization process, thereby obtaining a high-purity anhydrosugar alcohol.

<Explanation on symbols>

| | |
|---|---|
| 100: reactor unit | 110: raw material supply inlet |
| 120: unreacted raw material and by-product discharge outlet | |
| 130: product discharge outlet | 140: dispenser |
| 200: condenser | 300: separation/recovery means |
| 400: heating means | 410: heating media charge inlet |
| 420: heating media discharge outlet | |
| 500: pressure reducing means | |

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, it has been found that, if an anhydrosugar alcohol is produced by heating a reactor while supplying a sugar alcohol to the reactor, and, at the same time, the anhydrosugar alcohol is separated by distillation, after which melt crystallization is performed, a high-purity anhydrosugar alcohol can be produced in high yield even by a simple process and apparatus.

Therefore, in one aspect, the present invention is directed to a method of preparing and purifying anhydrosugar alcohol, the method comprises: reacting a sugar alcohol in a presence of an acid catalyst in a reactor, and at the same time, evaporating a reaction product; cooling an evaporated product, thereby obtaining a crude anhydrosugar alcohol; and introducing the crude anhydrosugar alcohol into a melt crystallization process, thereby obtaining a high-purity anhydrosugar alcohol.

Specific processes of the method for production and purification of anhydrosugar alcohol according to the present invention will now be described.

Figure 1:
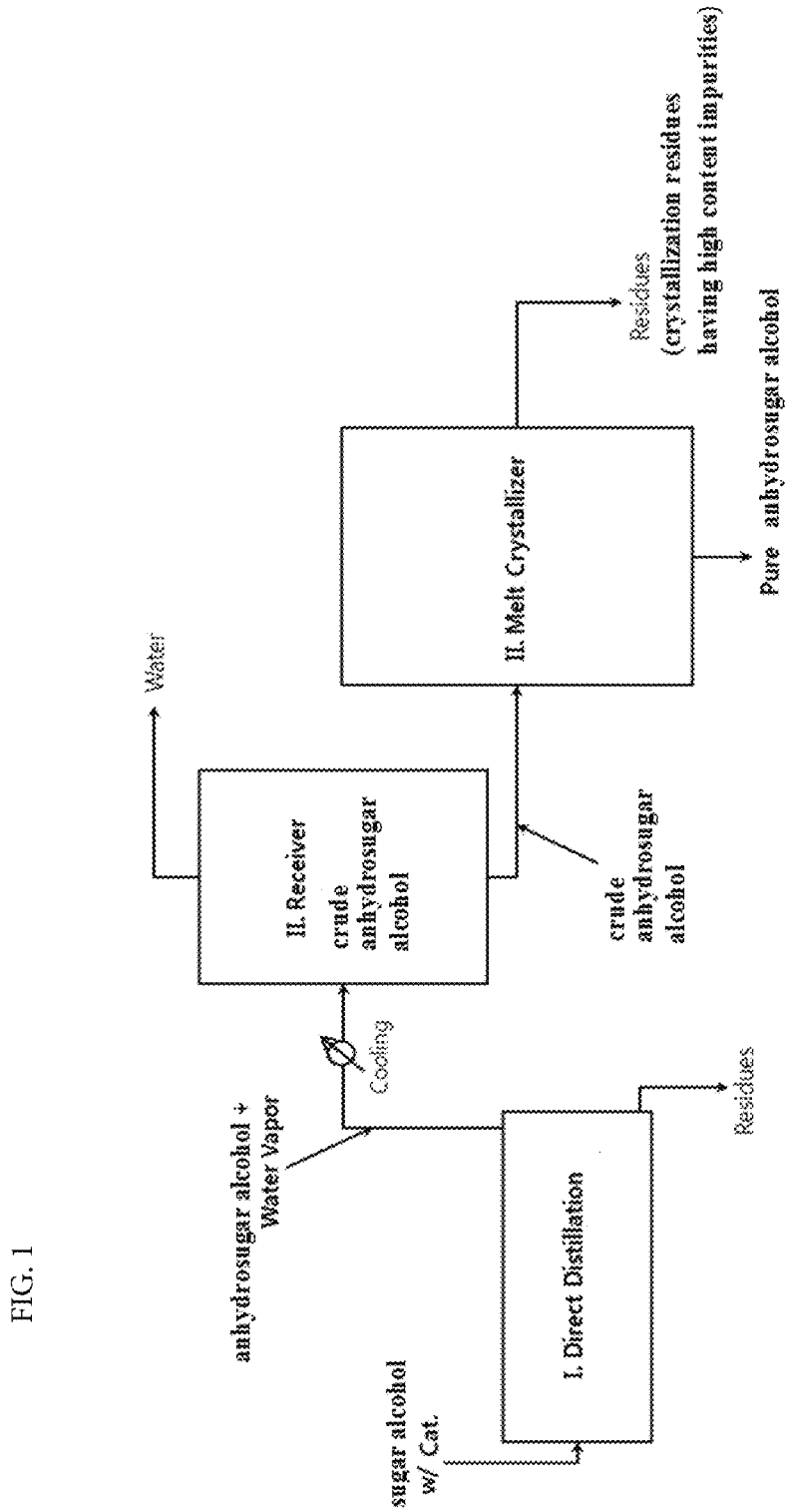
FIG. 1 is a flow chart schematically showing a method for producing and purifying anhydrosugar alcohol according to one embodiment of the present invention.

As shown in FIG. 1, according to the present invention, high-purity isosorbide is produced through melt crystallization after direct distillation.

1. Direct Distillation

Direct distillation is a process in which a reaction that converts sorbitol to isosorbide and a process that separates produced isosorbide by distillation are simultaneously carried out in a single reactor.

The catalyst that is used in the present invention satisfies the following conditions:

(a) Boiling Point

A catalyst having a boiling point higher than the boiling point of isosorbide (160° C. at 10 mmHg) is selected in order to maintain the activity of the catalyst without evaporation of the catalyst during the reaction and to easily separate the catalyst from isosorbide in a purification process such as vacuum distillation. Namely, the selected catalyst has a boiling point of 160° C. or higher at 10 mmHg.

(b) Acidity ($pK_a$)

The catalyst that is used in the present invention has an acidity suitable for reducing the production of by-products, such as polymers or cokes, at high reaction temperature. To increase the yield of isosorbide, the catalyst may have a pKa range of −3.0 to 3.0, preferably −2.0 to 2.5, more preferably −1.0 to 1.9.

(3) Homogeneous Phase

The catalyst that is used in the present invention reacts at a homogeneous phase under reaction conditions to increase the efficiency of contact between the catalyst and the feed. To this end, the catalyst may have a melting point of 180° C. or lower, preferably 160° C. or lower, more preferably 140° C. or lower, particularly preferably 120° C. or lower.

The catalyst that is used in the present invention may be naphthalenesulfonic acid. Specific examples of naphthalenesulfonic acid include 2-naphthalenesulfonic acid and 1-naphthalenesulfonic acid, which are isomers produced by sulfonation of naphthalene. 2-naphthalenesulfonic acid satisfies the following conditions: $pK_a$=0.27, m.p.=91° C., and b.p.=391.6° C. (having a boiling point of 160° C. or higher at 10 mmHg), and 1-naphthalenesulfonic acid satisfies the following conditions: $pK_a$=0.17, m.p.=90° C., and b.p.=392° C.

The temperature of the reaction may range from 150° C. to 220° C., preferably from 170° C. to 190° C. If temperature of the reaction is lower than 150° C., the reaction time or the residence time may be very long, and if the temperature of the reaction is higher than 220° C., side reactions may be promoted to reduce the yield of isosorbide. In addition, the pressure of the reaction may be 1 to 50 torr, preferably 1 to 20 torr. If the reaction pressure is less than 1 torr, there may be a problem in that there is a significant increase in the ratio of process operation in accordance with a high vacuum, and if the reaction pressure exceeds 50 torr, there may be a problem in that the reaction rate is slow and yield is reduced.

In view of process efficiency, cost effectiveness increases as the amount of catalyst added decreases. The catalyst that is used in the present invention may be added in an amount of 0.01-10 parts by weight, preferably 0.1-5 parts by weight, more preferably 0.2-3 parts by weight, based on 100 parts by weight of sugar alcohol. If the catalyst is added in an amount of less than 0.01 parts by weight, there may be a problem in that the dehydration reaction is very time-consuming, and if the catalyst is added in an amount of more than 10 parts by weight, there may be a problem in that the production of sugar polymers as by-products increase and the economic efficiency decreases due to an increase in the amount of catalyst used.

In the present invention, the sugar alcohol may be hexitol. Specifically, it may be one or more selected from the group consisting of sorbitol, mannitol and iditol. Preferably, the sugar alcohol is sorbitol. The anhydrosugar alcohol may be isosorbide, isomannide, isoidide or the like. Preferably, the anhydrosugar alcohol is isosorbide.

The method for producing anhydrosugar alcohol according to the present invention may be performed in a batch or continuous manner. It may be performed in a continuous stirred tank reactor (CSTR), a plug flow reactor (PFR) or a batch reactor (BR).

Figure 9:
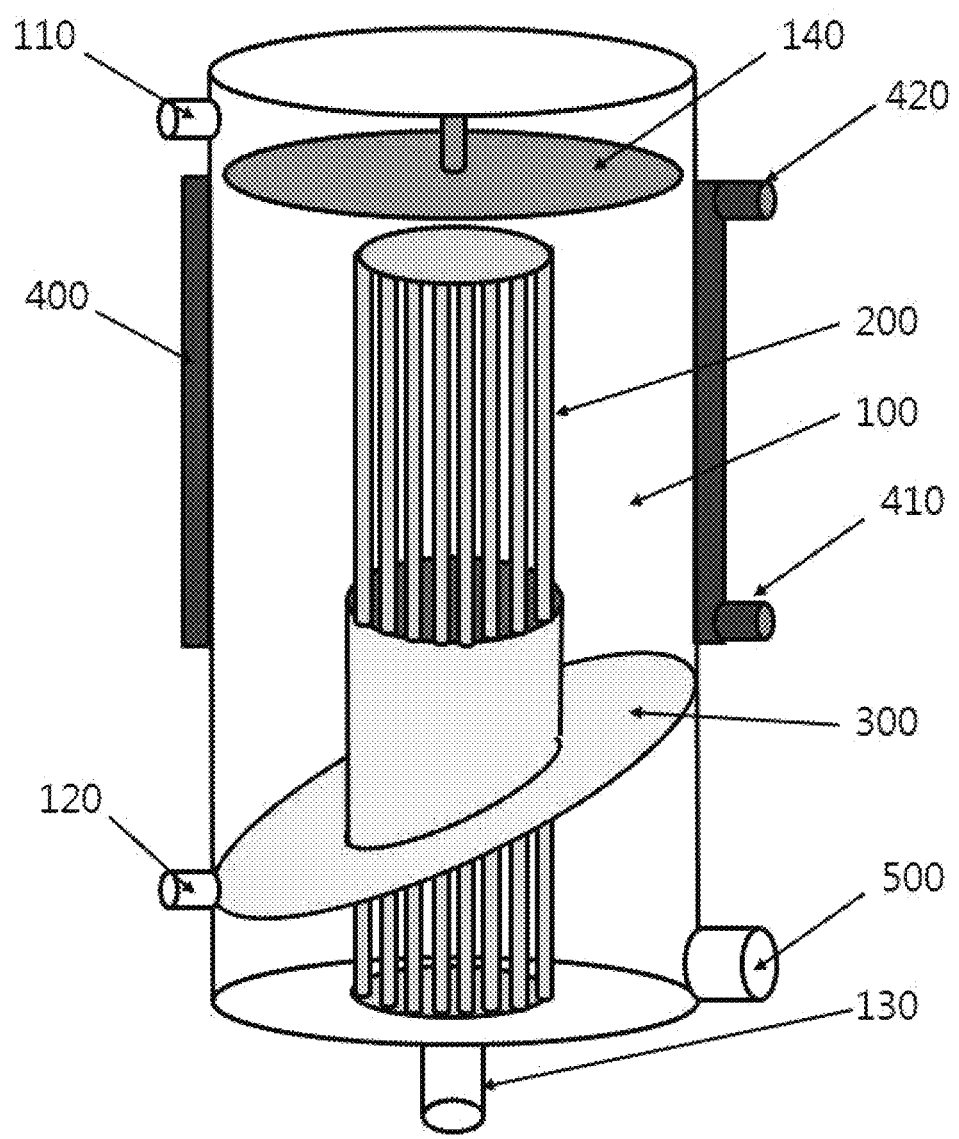
FIG. 9 shows the inside of a direct distillation apparatus according to one embodiment of the present invention.

In a preferred embodiment, as shown in FIG. 9, the reactor may comprise: (a) a reactor unit 100 including a dispenser 140 disposed at an upper portion thereof so as to allow a raw material to react while flowing down along an inner wall surface of the reactor; (b) a raw material supply inlet 110 disposed at one side of the upper portion of the reactor unit; (c) a means 300 for separating/recovering unreacted raw material and by-product, disposed in the reactor unit so as to be spaced apart from a bottom of the reactor unit by a predetermined distance; (d) a condenser 200 disposed at the inner center of the reactor unit so as to pass through the means for separating/recovering; (e) a means 500 disposed at one side of the reactor unit and configured to reduce the internal pressure of the reactor unit; and (f) a product outlet 130 disposed at the center of the bottom of the reactor unit and configured to discharge a product flowing down from the condenser 200.

2. Cooling of Evaporated Product

After direct distillation is carried out as described above, a mixture of impurity-containing crude anhydrosugar alcohol vapor and water vapor is obtained from the overhead of the reactor. A product obtained by cooling the mixture is referred to as "crude anhydrosugar alcohol". Particularly, when anhydrosugar alcohol is isosorbide, the mixture is referred to as crude isosorbide. The crude isosorbide is introduced into a melt crystallization process in which it is purified to a purity of 59% or higher, particularly 99.8% or higher. When a mixture of crude isosorbide vapor and water vapor is cooled to a temperature of 60° C. to 100° C., the water can be removed, and only a crude isosorbide residue can be obtained. The crude isosorbide melt has a purity of 90-99% (about 97%). A receiver has a temperature of 60 to 100° C., and is maintained at the same vacuum level as that of the reactor.

The water can mostly be removed in the receiver, and the water content of the melt can also be controlled by controlling the temperature of the receiver. Where an adsorption process is carried out before the melt crystallization process and the melt contains water, there is an advantage in that a separate adsorption solvent does not need to be added.

3. Melt Crystallization

The crude isosorbide is introduced into a melt crystallization process in which it is purified to a purity of 59% or higher, particularly 99.8% or higher. A melt crystallizer may have a temperature of −40° C. to 63° C., preferably −20° C. to 60° C., more preferably 30° C. to 60° C., most preferably 40° C. to 60° C. Because isosorbide has a melting point of about 63° C., it can be crystallized at a temperature of 63° C. or lower. If the crude isosorbide is cooled to lower than −40° C., there will be a problem in that the cooling efficiency decreases to increase the operating cost.

Melt crystallization that is carried out in the present invention may be falling film melt crystallization, static melt crystallization, or a combination of falling film melt crystallization and static melt crystallization.

Unreacted material (unreacted sugar alcohol) and intermediates (1,4-sorbitan, etc., when sugar alcohol is sorbitol), which are discharged from the bottom of the direct distillation reactor, may be recycled to the direct distillation process. Herein, unreacted material and intermediates, which are discharged from the bottom of the reactor, may be recycled after passage through an impurity removing means, and high-temperature/high-pressure vapor may be added to the feed that is recycled, in order to promote the additional conversion of unreacted material under hydrothermal conditions. In addition, the added vapor may serve as a stripping agent that helps isosorbide to evaporate in the direct distillation process.

In the present invention, the melt crystallization process may comprise the steps of: bringing the crude anhydrosugar alcohol into contact with a surface which is maintained at a temperature lower than the freezing point of pure anhydrosugar alcohol, thereby forming crystals; and increasing the temperature of the surface, which has the crystals formed thereon, to a temperature between the freezing point of pure anhydrosugar alcohol and the temperature at which the crystals of the crude anhydrosugar alcohol are formed.

In the temperature-increasing step, impurities trapped in the crystals are removed by diffusion to the surface of the crystals. The melt crystallization process may further comprise, after the temperature-increasing step, a step of increasing the temperature of the surface to a temperature higher than the freezing point of pure anhydrosugar alcohol to thereby melt the anhydrosugar alcohol formed on the surface.

3-1. Falling-Film Melt Crystallization

It is a method in which the crude isosorbide melt is allowed to flow onto a tubular layer which is maintained at low temperature, thereby forming isosorbide crystals. This method has advantages in that it is simple, easy to scale-up, and easy to operate.

Figure 2:
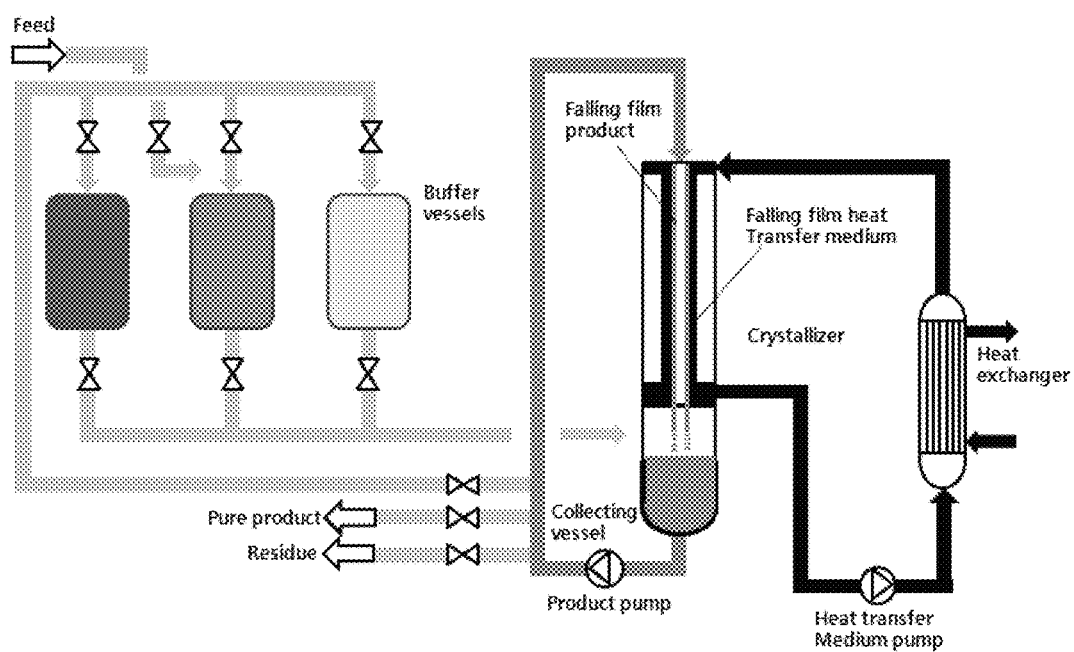
FIG. 2 schematically shows a falling-film melt crystallization apparatus according to one embodiment of the present invention.

FIG. 2 schematically shows an apparatus for falling-film melt crystallization according to the present invention. In the falling-film melt crystallization process, the crude anhydrosugar alcohol is allowed to flow to a surface which is maintained at a temperature lower than the freezing point of pure anhydrosugar alcohol, thereby forming crystals.

Figure 3:
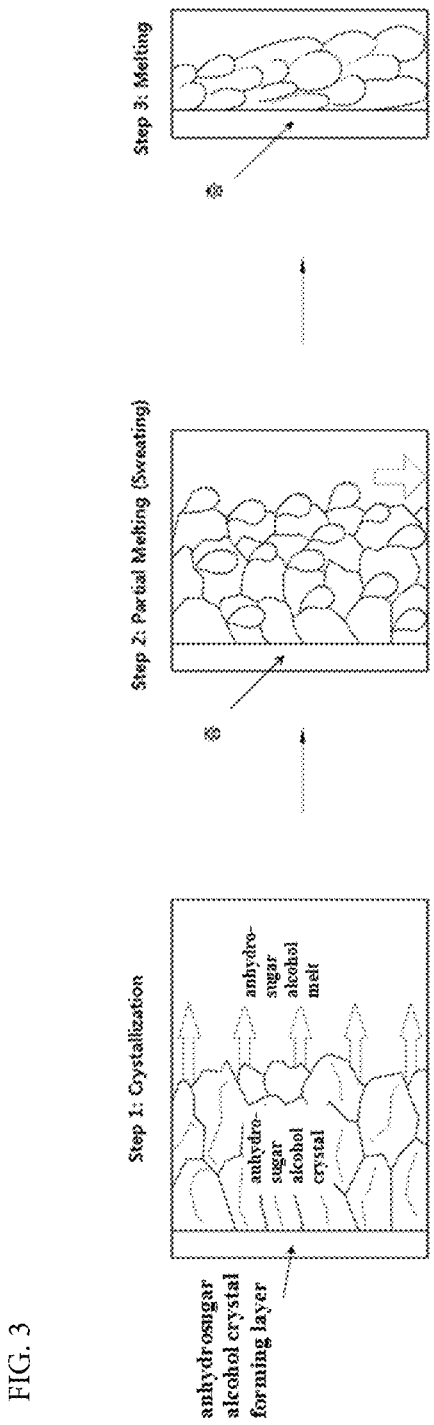
FIG. 3 shows the sequential steps of a falling-film melt crystallization process according to one embodiment of the present invention.

As shown in FIG. 3, the falling-film melt crystallization process has the following three steps in which crystals are formed by temperature control: crystallization→partial melting (sweating)→melting.

Step 1: Crystallization

Because isosorbide has a melting point of about 63° C., it can be crystallized at a temperature of 63° C. or lower. If the crude isosorbide is cooled to lower than −40° C., there will be a problem in that the cooling efficiency decreases to increase the operating cost. For this reason, the temperature of the surface which has isosorbide crystals formed thereon may be −40° C. to 63° C., preferably 30° C. to 60° C., more preferably 40° C. to 60° C.

Step 2: Partial Melting

When the isosorbide crystals are formed, impurities can be inserted into the crystals. Thus, when the layer temperature is increased to a temperature (40 to 60° C.) slightly higher than the temperature at which the crystals are formed, the impurities will have flowability. The impurities having flowability will be pushed out and removed from the crystal surface, and the purity of the isosorbide will further increase.

Step 3: Melting

In this step, the temperature of the layer is increased to a temperature equal to or higher than the melting point (60° C.) of isosorbide, thereby melting and recovering the isosorbide crystals. The melting point of the isosorbide crystals is preferably 60 to 90° C., more preferably 60 to 80° C.

3-2. Static Melt Crystallization

Static melt crystallization is a method in which the crude isosorbide melt is placed in a vessel and a plate through heat transfer medium (HTM) is circulated is brought into contact with the crude isosorbide melt, thereby forming isosorbide crystals.

The principle according to which the isosorbide crystals are formed is the same as that of falling-film melt crystallization. However, static melt crystallization has advantages in that even when the purity of the crude isosorbide melt is slightly low, it can be used, and in that the structure of the apparatus is very simple.

Figure 4:
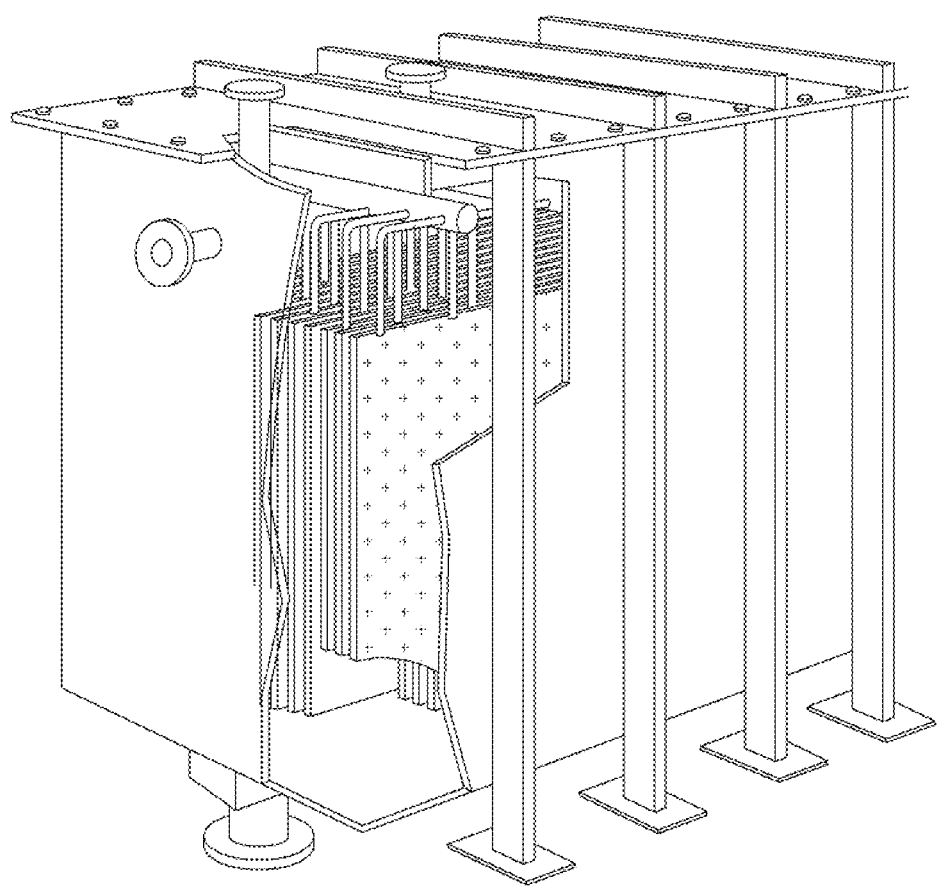
FIG. 4 schematically shows a static melt crystallization apparatus according to one embodiment of the present invention.

FIG. 4 schematically shows an apparatus for static melt crystallization according to the present invention. In the static melt crystallization process, an object whose surface temperature is maintained at a temperature lower than the freezing point of pure anhydrosugar alcohol is brought into contact with the crude anhydrosugar alcohol in a vessel containing the crude anhydrosugar alcohol, thereby forming crystals on the surface of the object.

Figure 5:
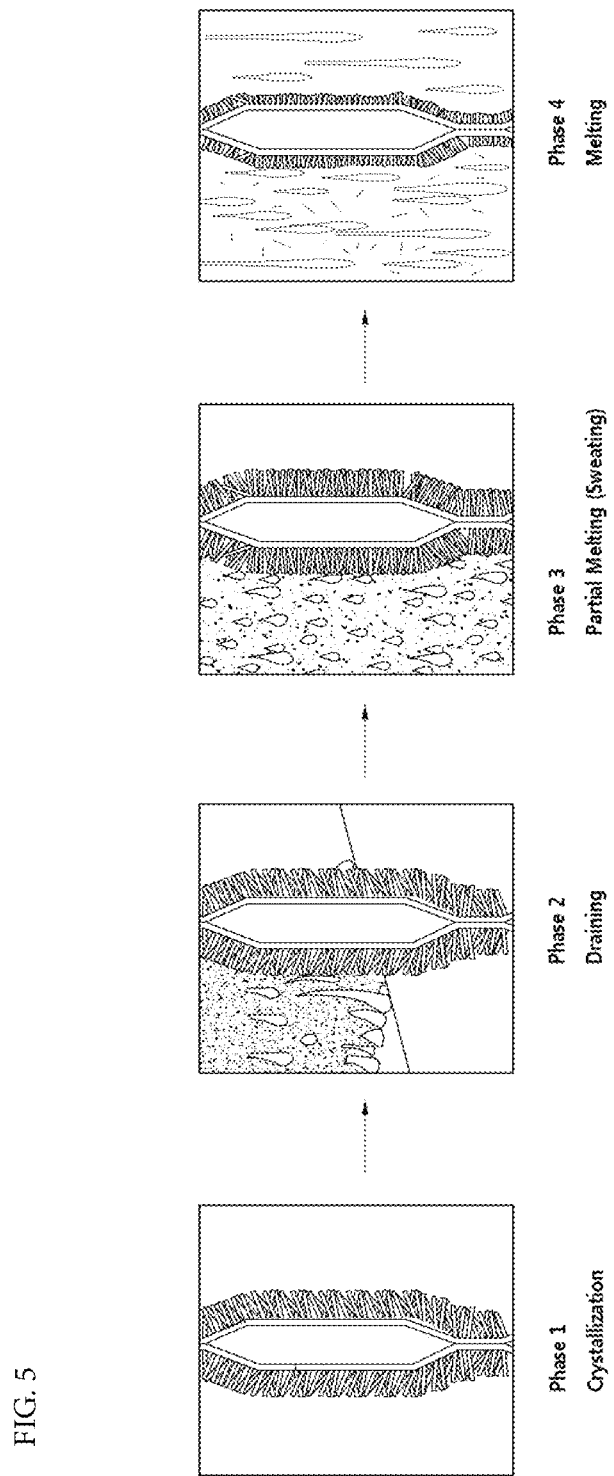
FIG. 5 shows the sequential steps of a static melt crystallization process according to one embodiment of the present invention.

As shown in FIG. 5, the static melt crystallization process comprises the following sequential steps: crystallization, draining, partial melting (sweating), and melting.

Herein, the melt crystallization may be a combination of falling-film melt crystallization and static melt crystallization.

In another aspect, the present invention is directed to a method of preparing and purifying anhydrosugar alcohol, the method comprises: reacting a sugar alcohol in a presence of an acid catalyst in a reactor, and at the same time, evaporating a reaction product; cooling an evaporated product, thereby obtaining a crude anhydrosugar alcohol; adsorbing the crude anhydrosugar alcohol; and introducing an adsorbed crude anhydrosugar alcohol into a melt crystallization process, thereby obtaining a high-purity anhydrosugar alcohol.

Figure 6:
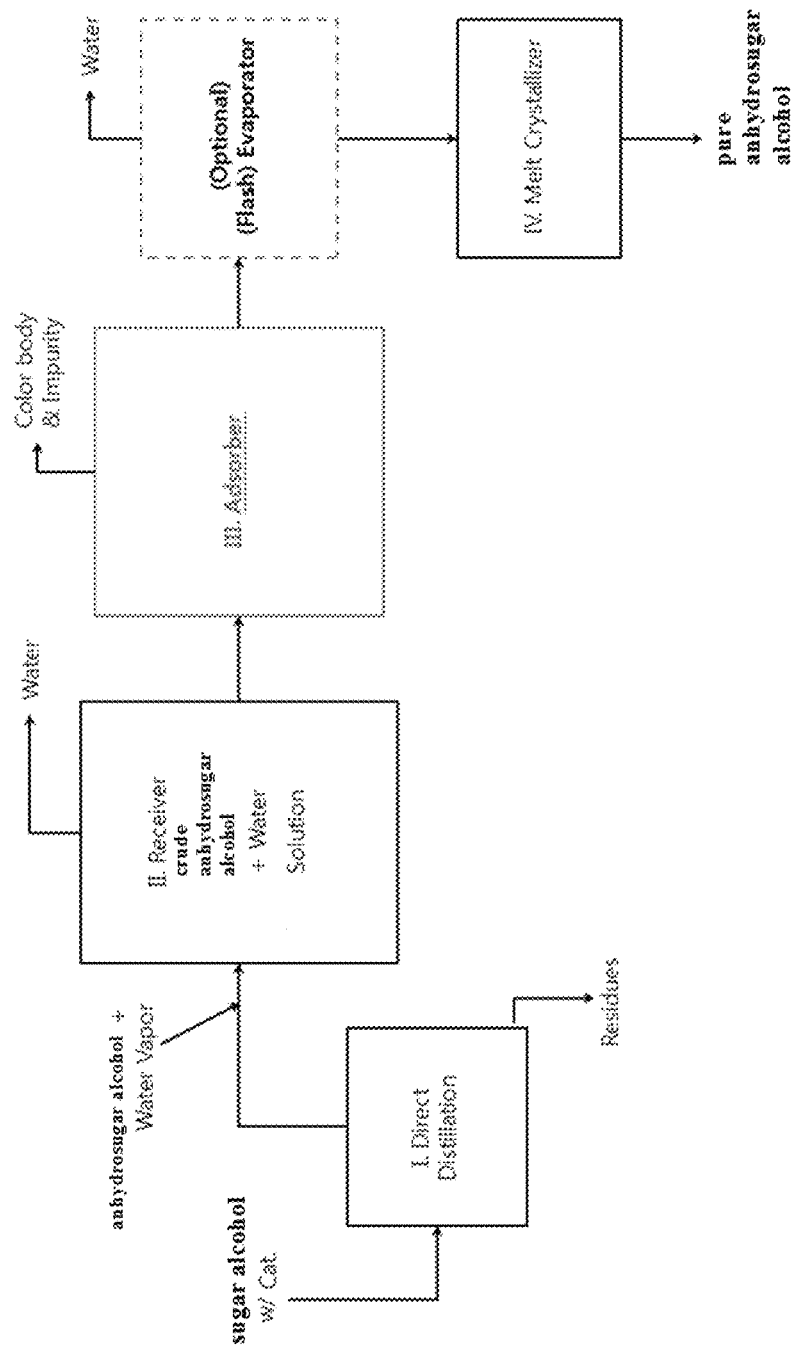
FIG. 6 is a flow chart schematically showing a method for production and purification of anhydrosugar alcohol according to one embodiment of the present invention, which further comprises an adsorption process.

In other words, in the present invention, the purity of anhydrosugar alcohol can further be increased by carrying out an adsorption process between direct distillation and melt crystallization by use of water contained in the melt as an adsorption solvent without adding a separate adsorption solvent (see FIG. 6). The adsorption process may be carried out at a temperature between room temperature and 60° C. and atmospheric pressure. When the temperature of an overhead receiver is controlled to a temperature between room temperature and 60° C., a solution containing isosorbide and water and having a water content of 1-30 wt % can be recovered without completely removing the water. The water serves as a solvent or a diluent in the adsorption process, and thus water does not need to be separately added for crystallization. At a temperature of 63° C., isosorbide becomes liquid and has high viscosity. For this reason, in prior technologies, it was required to add a solvent before carrying out the adsorption process. However, in the present invention, an isosorbide solution containing water can be prepared by controlling the temperature of the direct distillation receiver. Thus, the process is simple, and the operating and equipment costs can be reduced.

The adsorption process is performed by passing the solution containing isosorbide and water through an adsorbent, such as activated carbon, ion exchange resin or a combination thereof, to remove a color body and impurities. Although the kind of adsorbent that is used in the present invention is not limited, activated carbon is preferably used, and a combination of ion exchange resin and activated carbon may also be used. For example, activated carbon adsorption may be performed after ion exchange resin adsorption, and vice versa. To remove water contained in the product resulting from the adsorption process, an evaporation process such as flash evaporation may optionally be carried out.

The reaction residue (direct distillation (DD) residue) that is obtained from the bottom of the direct distillation process contains unreacted sugar alcohol, intermediates, and impurities, including a sugar alcohol polymer/oligomer and carbonized materials. Namely, the direct distillation residue contains: 1) unreacted sorbitol; 2) intermediates, including 1,4-sorbitan and the like; 3) a polymer/oligomer; and 4) carbonized materials.

As the reaction temperature and the reaction time are increased, the amount of unreacted material and intermediates decreases, but the amount of polymer/oligomer and carbonized materials increases. If the amount of polymer/oligomer and carbonized materials increases, the yield of isosorbide will decrease, and the viscosity of the residue will increase to make a continuous operation difficult. In severe cases, the polymer/oligomer and the like will be carbonized, and thus they will adhere to the wall surface and outlet of the reactor and result in shutdown of the reactor.

For this reason, it is required to reduce the residence time (reaction time) in the direct distillation reactor to thereby inhibit the formation of polymer/oligomer and carbonized materials, and it is important to recycle unreacted material and intermediates for additional conversion to thereby increase the yield of isosorbide. When the reaction temperature in direct distillation is reduced, the distillation of isosorbide is difficult, and for this reason, it is not easy to control the reaction temperature.

Figure 7:
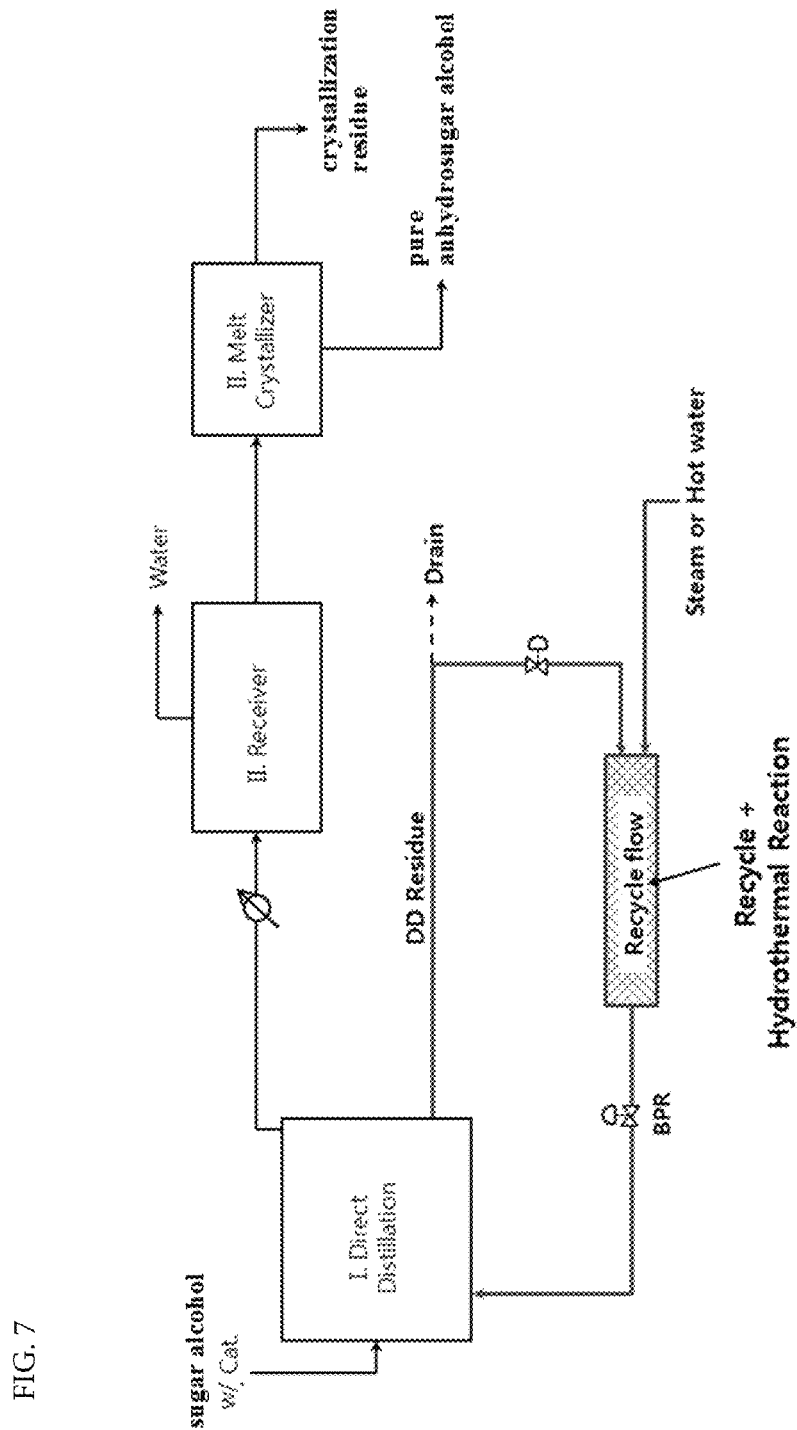
FIG. 7 shows a flow chart schematically showing a method for production and purification of anhydrosugar alcohol according to one embodiment of the present invention, which further comprises a recycle process.

In the present invention, unreacted material and intermediates, which are discharged from the bottom of the reactor, can be recycled to the reactor. As shown in FIG. 7, when the residue from the bottom of the direct distillation process is recycled to the reactor, high-temperature/high-pressure steam or hot water may be added to a recycle flow to induce additional conversion of unreacted material and intermediates. A hydrothermal reaction may be performed simultaneously with the recycle.

Direct distillation is a vacuum process. For this reason, in order to add high-temperature/high-pressure steam or hot water, a back pressure regulator (BPR) is installed in front of or behind the recycle flow to maintain the inside of the direct distillation reactor at a vacuum level, and the direct distillation residue is mixed with high-temperature/high-pressure steam or hot water.

The recycle flow is maintained at a temperature of 150 to 300° C., preferably 170 to 250° C., which is higher than the internal temperature of the direct distillation reactor. The recycle flow is maintained at a pressure equal to or higher than the saturated water vapor pressure at the corresponding temperature. For example, the recycle flow is maintained at 4.76 bar or higher at 150° C. and maintained at 85.81 bar or higher at 300° C.

In the present invention, high-temperature/high-pressure steam or hot water can perform three functions as follows.

First, because the internal pressure of the recycle flow is maintained at a pressure equal to or higher than the saturated water vapor pressure, high-temperature liquid water exists in the recycle flow. High-temperature liquid water can function as an acid catalyst by self-ionization, and high-temperature liquid water together with a naphthalenesulfonic acid catalyst promotes a reaction that converts unreacted material and a 1,4-sorbitan intermediate to isosorbide.

In other words, in the direct distillation reactor, isosorbide is formed by a vacuum reaction in the presence of a naphthalenesulfonic acid catalyst, and in the recycle flow, isosorbide is additionally formed in the presence of a naphthalenesulfonic acid catalyst together with hot-temperature/high-pressure hot water. The recycle flow has an advantage in that, even when the recycle flow is maintained at a temperature higher than the internal temperature of the direct distillation reactor, steam or hot water can dilute the residue to thereby inhibit carbonization of the residue.

The reason why a vacuum reaction is applied to a conventional reaction that converts sorbitol to isosorbide by dehydration is to continuously remove water from the reactant, because water molecules resulting from dehydration reduce the concentration of a catalyst and interfere with the reaction. Thus, when the reaction is carried out at a vacuum level of about 10 mmHg in the presence of sulfuric acid, the reaction can be carried out even at a low temperature of about 120 to 140° C., because the amount of water that interferes with the reaction is small. On the other hand, a high-pressure reaction in which water is not removed requires a higher reaction temperature even in the presence of the same catalyst as used in the vacuum reaction, because the amount of water (that interferes with the reaction) in the high-pressure reaction is larger than that in the vacuum reaction. However, when the reaction temperature is increased, the amount of side reactions, such as decomposition, polymerization and char formation, will increase. Particularly, when a strong acid catalyst such as sulfuric acid is used, a large amount of side reactions will occur at high temperature. Thus, it is important to select an effective catalyst which is less acidic than sulfuric acid and which can suppress side reactions at high temperature. Therefore, in the present invention, the yield of isosorbide in a dehydration reaction that converts sorbitol to isosorbide under the high-temperature and high-pressure conditions of temperature of 160° C. to 260° C. and pressure of 10 bar to 50 bar could be increased by using a catalyst which has a boiling point higher than that of isosorbide so as to maintain its activity without evaporation during the reaction and which can be easily separated from isosorbide in a purification process such as vacuum distillation and which forms a homogeneous phase under the reaction conditions to increase the efficiency of contact between the catalyst and the feed and which has an acidity suitable for reducing the production of by-products such as a polymers or cokes at high reaction temperature.

Second, the steam or hot water added to the recycle flow can additionally supply energy required for maintaining the internal temperature of the direct distillation reactor and for carrying out the dehydration reaction. The dehydration reaction that converts sorbitol to isosorbide is a weak endothermic reaction. In the direct distillation reactor which is maintained at a vacuum pressure, the water and isosorbide produced by the reaction are continuously distilled, and for this reason, phase change energy which is used for distillation, in addition to reaction heat, is continuously consumed. In the case of commercial processes, it is difficult to supply energy into the reactor through the outer wall of the reactor and to maintain the internal temperature of the reactor at a constant level.

However, in the present invention, the high-temperature steam or hot water added to the recycle flow supplies energy required for the reaction and phase change while it is introduced into the direct distillation reactor. Thus, there is an advantage in that the internal temperature of the direct distillation reactor can be maintained at a constant level.

Third, steam or hot water functions as a stripping agent that helps produced isosorbide to be distilled in the direct distillation reactor. Because isosorbide has a high boiling point, a high vacuum level is required to distill the isosorbide, and a special distillation apparatus such as a thin film evaporator is generally used. The present invention is characterized in that a reaction and a distillation process are simultaneously performed in a single reactor (direct distillation reactor) without using a thin film evaporator.

Steam or hot water can form an azeotrope with this isosorbide to thereby promote distillation of the isosorbide. In addition, when high-pressure steam or hot water in the recycle flow is introduced into the direct distillation reactor which is at a vacuum pressure, it can create a rapid boiling phenomenon to thereby further promote the distillation of isosorbide.

Meanwhile, a melt crystallization product that is discharged from the melt crystallizer may be recycled to the melt crystallization process, and a melt crystallization residue may be recycled to the reactor or the melt crystallization process.

Figure 8:
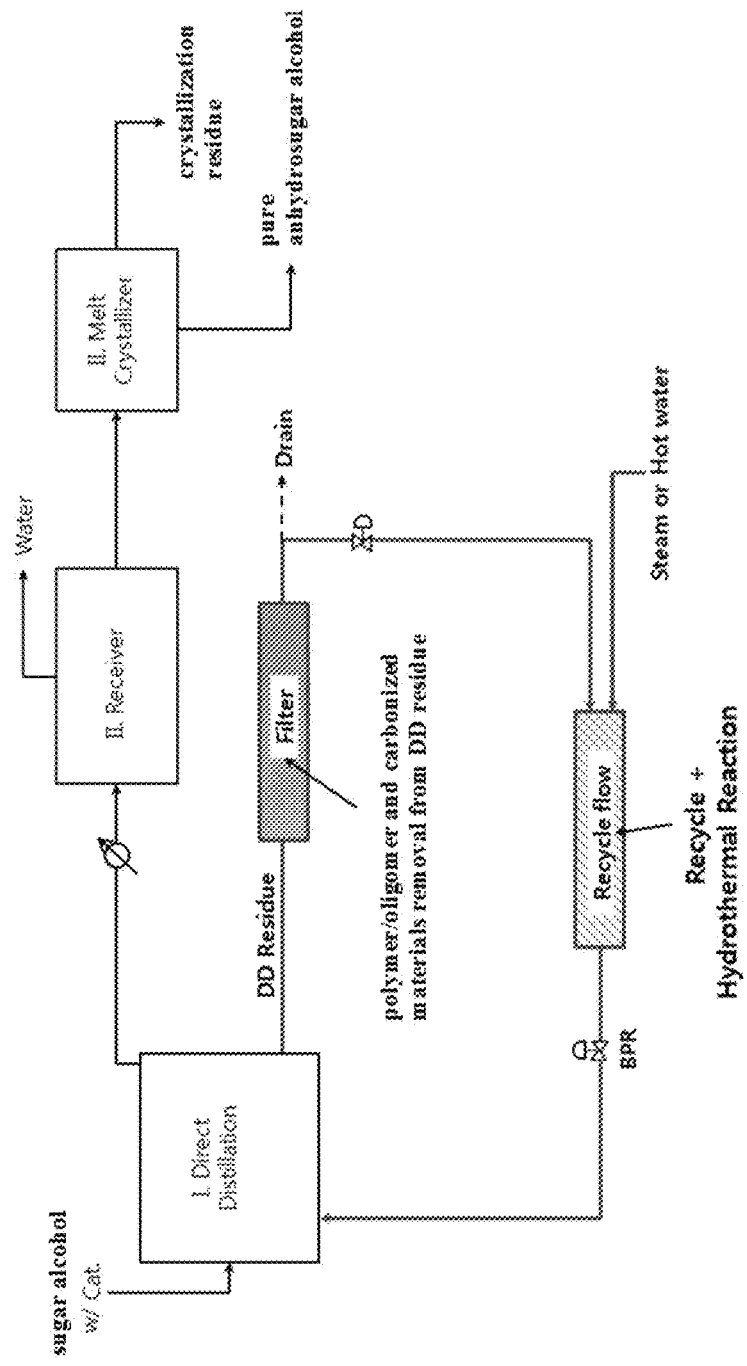
FIG. 8 shows a flow chart schematically showing a method for production and purification of anhydrosugar alcohol according to one embodiment of the present invention, which further comprises a recycle process that uses a filter.

In addition, as shown in FIG. 8, an impurity removing means such as a filter may be disposed between the outlet of the direct distillation reactor and the recycle flow so that only unreacted material and intermediates can be recycled after removal of the polymer/oligomer and carbonized materials contained in the direct distillation residue. The kind of filter is not particularly limited.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

500-1000 g of D-sorbitol (Aldrich) was introduced into a 1,000-mL reactor and dissolved at a reaction temperature of 110 to 200° C., and then 3.0 wt % of naphthalenesulfonic acid hydrate (Aldrich) was added thereto and stirred, and the reaction pressure was reduced to 5-10 mmHg. A material, which was evaporated and discharged through the top of the reactor for 2-5 hours, was defined as crude isosorbide. Crude isosorbide produced under various conditions was collected, and water was evaporated from the collected crude isosorbide in a rotary evaporator under the conditions of 90° C. and 30 mbar for 1 hour. Next, distilled water was added to the water-evaporated isosorbide to reach a water content of 2%.

The solution prepared as described above was introduced into a 1.5 L stirring tank, and a small amount of isosorbide powder was added thereto and stirred to form isosorbide crystals. When there was no change in the inside of the stirring tank after formation of the crystals, the solution excluding the crystals was removed, and the internal temperature of the stirring tank was increased to 47° C. to melt and remove some impurities trapped in the crystals or attached to the outside of the crystals.

The crystals obtained as described above and the solution before the crystallization step were diluted 25-fold with water, and analyzed by high-performance liquid chromatography (HPLC) system (Agilent; equipped with a REZEX monosaccharide column). As a result, the purity of isosorbide in the solution before crystallization was 95.1 wt %, and the purity of isosorbide after crystallization was 96.4 wt %.

Example 2

The solution prepared as described in Example 1 was crystallized in the same manner as described in Example 1. After formation of the crystals, the solution excluding the crystals was removed, and the internal temperature of the stirring tank was increased to 37° C. to melt out impurities.

The purity of the crystals obtained as described above and the composition of the solution used as the feed were analyzed according to the method described in Example 1. As a result, the purity of isosorbide in the solution before crystallization was 91.5 wt %, and the purity of isosorbide after crystallization was 94.2 wt %.

Example 3

Crude isosorbide was prepared in the same manner as described in Example 1, and water was evaporated from the crude isosorbide. Then, distilled water was added to the water-evaporated isosorbide to reach a water content of 6 wt %.

The solution prepared as described above was crystallized in the same manner as described in Example 1, thereby obtaining crystals. However, the temperature of the stirring tank was increased to about 30° C. in order to remove impurities.

The purity of the isosorbide crystals obtained as described above was analyzed according to the method described in Example 1. As a result, the purity of isosorbide in the solution before crystallization was 96.1 wt %, and the purity of isosorbide after crystallization was 98.7 wt %.

Example 4

Crude isosorbide was prepared in the same manner as described in Example 1, and a color-developing material was adsorbed onto activated carbon. The activated carbon used was obtained by drying granule type activated carbon (GAC 1240; NORIT) in an oven at 150° C. for 8 hours or more. 130 g of activated carbon was densely packed into an STS tube having a diameter of 50 mm and a length of 150 mm, and then crude isosorbide was allowed to flow upward through the tube. The flow rate was 1 mL/min, and the flow was maintained for 10 days or more. The color of the crude isosorbide that passed through the adsorption column was measured by yellowness index (YI).

Figure 10:
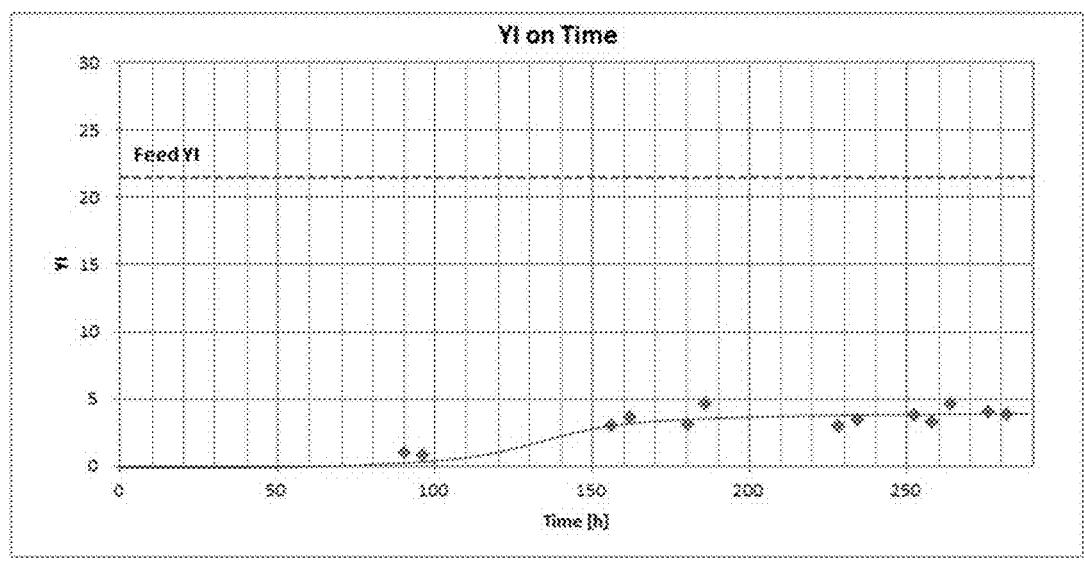
FIG. 10 is a graph showing the results of measuring the yellowness index (YI) of a crude isosorbide feed according to one embodiment of the present invention.

As shown in FIG. 10, the YI of the crude isosorbide used as the feed was 21.7, and the YI of the flow that passed through the adsorption column was 1 or less up to about 100 hours and 3-5 after 150 hours. The YI of the adsorption column was maintained at this level up to 12 days (=288 hours).

Example 5

Using ASPEN, a process of dehydrating sorbitol by a direct distillation process was simulated. An aqueous sorbitol solution was dried to obtain a feed containing 1 wt % of water. The feed was introduced into a first reactor at 110° C. and 8 torr and allowed to react for 90 minutes. The reaction product was introduced into a second rector at 180° C. and 8 torr and allowed to react for 30 minutes. In the first and second reactors, water and isosorbide were discharged through the top and obtained as a product.

The bottom flow of the second reactor was conditioned to have an isosorbide content of about 10% in order to maintain its flowability and was recycled to the reactor. 10 wt % of the bottom flow was wasted in order to prevent an oligomer and a polymer from being circulated and accumulated.

Example 6

A reaction process of dehydrating sorbitol was simulated in the same manner as described in Example 5. However, the bottom flow of the second reactor was recycled to the reactor after a hydrothermal reaction in Example 5.

Comparative Example 1

A reaction process of dehydrating sorbitol was simulated in the same manner as described in Example 5. However, the bottom flow of the reactor was not recycled, and isosorbide remaining in the bottom flow was evaporated under the conditions of 180° C. and 1 torr so as to be combined with the top product.

The yields of the products obtained in Examples 5 and 6 and Comparative Example 1 were calculated using the following equation, and the results of the calculation are shown in Table 1 below.

wt % yield=[weight of material produced/weight of sorbitol produced]×100

In all the cases, the yields of products other than isosorbide were 0.1 wt % or less, and thus were not specifically mentioned.

TABLE 1

| | Recycle flow | Hydrothermal reaction | Isosorbide yield |
|---|---|---|---|
| Example 5 | Reactor bottom | Not performed | 61.5 |
| Example 6 | Reactor bottom | Performed | 63.7 |
| Comparative Example 1 | Not present | Not performed | 60.1 |

As shown in Table 1 above, in the case of Examples 5 and 6 in which production and distillation of anhydrosugar alcohol were simultaneously performed, after which the residue obtained from the bottom of the reactor was recycled to the crystallization process while the melt crystallization process was performed, it was shown that the yield of the process for separation of anhydrosugar alcohol was increased. It is obvious that when a feed having an increased content of anhydrosugar alcohol is subjected to a crystallization process, it has improved purity under the same conditions, and thus the purity of anhydrosugar alcohol is also improved.

INDUSTRIAL APPLICABILITY

As described above, according to the present invention, high-purity anhydrosugar alcohol can be produced in high yield, and a thin film evaporation process that incurs high equipment and operating costs can be omitted. Furthermore, an ion exchange step can be omitted due to omission of neutralization of impure anhydrosugar alcohol, and thus sodium-free anhydrosugar alcohol can be produced. In addition, due to a decrease in the absolute amount of impurities in crude isosorbide, the load of a latter separation process such as an activated carbon bed process can be reduced, thus reducing the operating cost for the reaction and the equipment cost for the reactor.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing and purifying anhydrosugar alcohol, the method comprising:
reacting a sugar alcohol in a presence of an acid catalyst in a reactor, and at the same time, evaporating a reaction product;
cooling an evaporated product, thereby obtaining a crude anhydrosugar alcohol; and
introducing the crude anhydrosugar alcohol into a melt crystallization process, thereby obtaining a high-purity anhydrosugar alcohol,
wherein a reaction residue discharged from a bottom of the reactor is recycled to the reactor and high temperature vapor is added to a recycled feed to induce an additional conversion of unreacted materials and intermediates.

2. A method of preparing and purifying anhydrosugar alcohol, the method comprising:
reacting a sugar alcohol in a presence of an acid catalyst in a reactor, and at the same time, evaporating a reaction product;
cooling an evaporated product, thereby obtaining a crude anhydrosugar alcohol;
adsorbing the crude anhydrosugar alcohol; and
introducing an adsorbed crude anhydrosugar alcohol into a melt crystallization process, thereby obtaining a high-purity anhydrosugar alcohol,
wherein a reaction residue discharged from a bottom of the reactor is recycled to the reactor and high temperature vapor is added to a recycled feed to induce an additional conversion of unreacted materials and intermediates.

3. The method of claim 1, wherein the acid catalyst has a boiling point of 160° C. or higher at 10 mmHg and pKa range of −3.0 to 3.0, and reacts at a homogeneous phase.

4. The method of claim 3, wherein the acid catalyst is naphthalenesulfonic acid.

5. The method of claim 1, wherein a temperature of the reactor is 150° C. to 220° C. and a pressure of the reactor is 1 to 50 torr.

6. The method of claim 1, wherein the anhydrosugar alcohol is isosorbide, and the sugar alcohol is sorbitol.

7. The method of claim 1, wherein the reactor comprises:
(a) a reactor unit including a dispenser disposed at an upper portion thereof for reacting a raw material with flowing down along an inner wall side of the reactor;
(b) a raw material supply unit disposed at one side of the upper portion of the reactor unit;
(c) a means for separating/recovering unreacted raw material and by-product, disposed in the reactor unit spaced apart from a bottom of the reactor unit by a predetermined distance;
(d) a condenser disposed at the inner center of the reactor unit to pass through the means for separating/recovering;
(e) a means disposed at one side of the reactor unit to reduce an internal pressure of the reactor unit; and
(f) a product outlet disposed at a bottom center of the reactor unit to discharge a product flowing down from the condenser.

8. The method of claim 1, wherein the melt crystallization process comprises:
contacting the crude anhydrosugar alcohol into surface maintained at a temperature lower than a freezing point of pure anhydrosugar alcohol, thereby forming crystals; and
increasing a temperature of the surface on which the crystals are formed, to a temperature between the freezing point of pure anhydrosugar alcohol and the temperature at which the crystals of the crude anhydrosugar alcohol are formed.

9. The method of claim 8, wherein in a temperature-increasing step, impurities trapped in the crystals are removed by diffusion to the surface of the crystals, and
wherein the melt crystallization process further comprises, after the temperature-increasing step, a step of increasing the temperature of the surface to at least the freezing point of pure anhydrosugar alcohol to thereby melting the anhydrosugar alcohol formed on the surface.

10. The method of claim 8, wherein the temperature of the surface on which the crystals are formed is −40° C. to 63° C.

11. The method of claim 1, wherein the melt crystallization is falling film melt crystallization, static melt crystallization or a combination thereof.

12. The method of claim 11, wherein the falling film melt crystallization comprises forming crystals by flowing the crude anhydrosugar alcohol to a surface which is maintained at a temperature lower than a freezing point of pure anhydrosugar alcohol, and
wherein the static melt crystallization comprises contacting an object whose surface temperature is maintained at a temperature lower than the freezing point of pure anhydrosugar alcohol with the crude anhydrosugar alcohol in a vessel storing the crude anhydrosugar alcohol, thereby forming crystals on the surface of the object.

13. The method of claim 1, wherein a residue in the melt crystallization is recycled to the reactor or the melt crystallization.

14. The method of claim 1, wherein high pressure vapor is added to the recycled feed to induce an additional conversion of unreacted materials and intermediates.

15. The method of claim 1, wherein the reaction residue discharged from the bottom of the reactor is recycled after passing through an impurity removing means.

16. The method of claim 15, wherein the impurity removing means is a filter.

17. The method of claim 15, wherein the reaction residue comprises unreacted sugar alcohol, intermediates, a sugar alcohol polymer, a sugar alcohol oligomer, carbonized materials, or a mixture thereof, and the impurity comprises a sugar alcohol polymer, a sugar alcohol oligomer, carbonized materials, or a mixture thereof.

18. The method of claim 2, wherein high pressure vapor is added to the recycled feed to induce an additional conversion of unreacted materials and intermediates.

19. The method of claim 18, wherein the recycled feed is maintained at a pressure of at least saturated water vapor pressure.

20. The method of claim 18, wherein a temperature of the recycled feed is higher than that of the reactor.

21. The method of claim 18, wherein the temperature of the recycled feed is 150 to 300° C.

22. The method of claim 18, wherein a back pressure regulator is installed in front of or behind the recycled feed.

23. The method of claim 2, wherein the evaporated product is cooled to a temperature between room temperature and 60° C. to obtain a crude anhydrosugar alcohol containing water of 1-30 wt %.

24. The method of claim 2, wherein a flash evaporation process is additionally carried out after the adsorption process to remove water.

25. The method of claim 2, wherein the adsorption process is performed by activated carbon, ion exchange resin or a combination thereof.

* * * * *